(12) United States Patent
Laitinen et al.

(10) Patent No.: US 8,542,349 B2
(45) Date of Patent: Sep. 24, 2013

(54) ARRANGEMENT AND A METHOD FOR CONTROLLING A MEASUREMENT HEAD OF AN OPTICAL MEASUREMENT INSTRUMENT

(75) Inventors: Jyrki Laitinen, Kuusisto (FI); Markku Ojala, Turku (FI); Jarkko Sarmaala, Turku (FI); Christer Isaksson, Turku (FI)

(73) Assignee: Perkinelmer Singapore Pte. Ltd., Singapore (SG)

( * ) Notice: Subject to any disclaimer, the term of this patent is extended or adjusted under 35 U.S.C. 154(b) by 119 days.

(21) Appl. No.: 13/145,652

(22) PCT Filed: Jan. 18, 2010

(86) PCT No.: PCT/FI2010/050022
§ 371 (c)(1),
(2), (4) Date: Sep. 20, 2011

(87) PCT Pub. No.: WO2010/084244
PCT Pub. Date: Jul. 29, 2010

(65) Prior Publication Data
US 2012/0002190 A1 Jan. 5, 2012

Related U.S. Application Data

(60) Provisional application No. 61/149,557, filed on Feb. 3, 2009.

(30) Foreign Application Priority Data

Jan. 26, 2009 (FI) .................. 20095064 U

(51) Int. Cl.
*G01B 11/16* (2006.01)
(52) U.S. Cl.
USPC ............................ 356/32; 356/34

(58) Field of Classification Search
USPC .............. 356/32–35.5, 244, 246; 359/368, 359/379, 381–382, 388, 362, 390; 382/144–147
See application file for complete search history.

(56) References Cited

U.S. PATENT DOCUMENTS

| 7,556,968 B2 * | 7/2009 | Ando et al. .................. 436/165 |
| 2002/0163715 A1 | 11/2002 | Engelhardt et al. |
| 2006/0261829 A1 * | 11/2006 | Hanson et al. .............. 324/754 |

FOREIGN PATENT DOCUMENTS

| EP | 0 030 148 A1 | 6/1981 |
| EP | 0 987 540 A2 | 3/2000 |
| EP | 2 006 662 A2 | 12/2008 |
| JP | 2002156383 A | 5/2002 |
| WO | 00/04364 A2 | 1/2000 |
| WO | 2004003504 A2 | 1/2004 |

OTHER PUBLICATIONS

Finnish Search Report, dated Oct. 28, 2009, from corresponding Finnish application.
International Search Report, dated May 7, 2010, from corresponding PCT application.

* cited by examiner

*Primary Examiner* — Tri T Ton
(74) *Attorney, Agent, or Firm* — Young & Thompson

(57) ABSTRACT

An optical measurement instrument includes a measurement head and mechanical support elements arranged to support a sample well plate. The measurement head is moved towards the sample well plate and, after the measurement head has touched the sample well plate, the measurement head is moved backwards away from the sample well plate so as to provide a desired distance between the measurement head and the sample well plate. A sensor device is attached to the mechanical support elements and arranged detect a mechanical effect occurring in the mechanical support elements due to force directed by the measurement head to the sample well plate. Hence, the situation in which the measurement head touches the sample well plate can be detected without a need to provide the measurement head with a force sensor. This is advantageous because the measurement head can be a changeable module of the optical measurement instrument.

17 Claims, 4 Drawing Sheets

ARRANGEMENT AND A METHOD FOR CONTROLLING A MEASUREMENT HEAD OF AN OPTICAL MEASUREMENT INSTRUMENT

FIELD OF THE INVENTION

The invention relates to an arrangement and a method for controlling a measurement head of an optical measurement instrument. An optical measurement can be, for example but not necessarily, an absorption measurement, a photoluminescence measurement, or a chemiluminescence measurement. Furthermore, the invention relates to an optical measurement instrument.

BACKGROUND

The work in analytical biochemical laboratories and in clinical laboratories is often based on different tags or labels coupled on macromolecules under inspection. Typical labels used are different radioactive isotopes, enzymes, different fluorescent molecules and e.g. fluorescent chelates of rare earth metals. Detection of enzyme labels can be performed by utilizing its natural biochemical function, i.e. to alter the physical properties of molecules. In enzyme immunoassays colourless substances are catalysed by enzyme to colourful substances or non-fluorescent substances to fluorescent substances.

The colourful substances can be measured with absorption measurement, i.e. photometric measurement. In the absorption measurement the intensity of filtered and stabilized beam is first measured without any sample and then the sample inside one plate is measured. The absorbance i.e. the absorption values are then calculated.

The fluorescent substances can be measured with fluorescent measurement that is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies.

A further measurement method is chemiluminescence measurement where emission of a substance is measured from a sample without excitation by illumination. Thus a photoluminometer suitable for photoluminescence measurements can also be used as a chemiluminometer.

Further, there is an analysing method called Amplified Luminescent Proximity Homogeneous Assay or AlphaScreen™. The function of the AlphaScreen™ method is based on the use of small beads that attach to the molecules under study. There are two types of beads that are coated with a material acting either as a donor or acceptor of singlet-state oxygen. The measurement starts, when the liquid sample is illuminated by light with a suitable wavelength e.g. 680 nm. After this, the material in the donor bead converts ambient oxygen into singlet-state oxygen. The single-state molecules have a short lifetime and they can reach only about a 200 nm distance by diffusion in the liquid. If the chemical reaction in question has taken place, both the donor and acceptor beads are bound to the same molecule and so they are sufficiently close to each other. In this case the singlet-state oxygen may reach the acceptor bead where a series of reactions is started. As the last phase of the reaction the coating material in the acceptor beads emits photons in the 500-700 nm range. If the chemical reaction has not taken place the singlet-state oxygen cannot reach the acceptor bead and the emission light is not detected. By measuring the intensity of light it is possible to conclude the efficiency of the chemical reaction.

An optical measurement instrument suitable for performing some or all of the measurements of the kind described above comprises typically at least one excitation light source for producing excitation beams to one or more samples to be measured at each time. Each excitation light source can be for example a flash lamp or a laser source. An optical path from an excitation light source to a sample may contain for example lenses, fibers, mirrors, dichroic mirrors, optical filters, monochromators and/or other optical elements. The optical measurement instrument further comprises at least one detector for detecting emission beams emitted by the samples to be measured at each time, and for producing detection signals responsive to the detected emission beams. Each detector can be for example a photodiode or a photomultiplier tube. An optical path from the sample to the detector may contain for example lenses, fibers, mirrors, dichroic mirrors, optical filters, monochromators, and/or other optical elements. The optical measurement instrument may further comprise a processing device for producing a measurement result for each sample to be measured on the basis of the detection signal related to that sample. Each sample to be measured is stored in one of a plurality of sample wells that are built on a sample well plate, e.g. a microtitration plate. The optical measurement instrument may comprise, for example, a movable sledge adapted to receive the sample well plate. Due to the fact that the sample well plate is movable, the samples can be measured in a temporally successive manner so that each sample is in turn the sample that is currently being measured and/or excited. In this document an optical module or element that is arranged to direct an excitation beam to a sample and/or to collect emission beam from a sample is called a measurement head. In other words, the measurement head is an optical interface of the optical measurement instrument with respect to a sample to be measured and/or excited.

In order to provide appropriate optical measurements, the distance from the measurement head to a sample to be measured and/or excited has to be adjusted with a sufficient accuracy. For example in conjunction with many optical measurements, an excitation beam has to be appropriately focused to the sample. The distance between the measurement head and the sample can be adjusted to a desired value for example by first moving the measurement head towards the sample well plate and, after the measurement head has touched the sample well plate, by moving the measurement head backwards away from the sample well plate with a pre-determined length of movement so as to provide the desired distance between the measurement head and the sample well plate. The situation in which the measurement head touches the sample well plate can be detected, for example, with a force sensor attached to the measurement head and arranged detect force directed by the measurement head to the sample well plate. An inconvenience related to a technical solution of the kind described above is that the measurement head can be a changeable module in which case each measurement head has to be provided with an own force sensor or, alternatively, the force sensor has to be moved from one measurement head to another measurement head every time when the measurement head is changed.

SUMMARY

In accordance with a first aspect of the invention, there is provided a new arrangement for controlling a measurement head of an optical measurement instrument, the measurement head being an optical interface of the optical measurement instrument with respect to a sample to be measured and/or excited, and the optical measurement instrument further comprising first mechanical support elements arranged to support a sample well plate to be received and second mechanical support elements arranged to support the measurement head and to allow a distance from the measurement head to the sample well plate to be changed. The arrangement according to the invention comprises:

a controller arranged make, in a situation in which the sample well plate is placed on the first mechanical support elements, the second mechanical support elements to move the measurement head towards the sample well plate and, as a response to a situation in which the measurement head touches the sample well plate, to move the measurement head backwards away from the sample well plate with a pre-determined length of movement so as to provide a pre-determined distance between the measurement head and the sample well plate, and a sensor device arranged to detect, in the situation in which the sample well plate is placed on the first mechanical support elements, the situation in which the measurement head touches the sample well plate, wherein the sensor device is attached to the first mechanical support elements and arranged to detect, in the situation in which the sample well plate is placed on the first mechanical support elements, a mechanical effect occurring in the first mechanical support elements due to force directed by the measurement head to the sample well plate when the measurement head touches the sample well plate.

The situation in which the measurement head touches the sample well plate can be detected without a need to provide the measurement head with a sensor. This is advantageous because the measurement head can be a changeable module of the optical measurement instrument and thus, using the arrangement according to the invention, there is no need to provide each measurement head with an own sensor or to move a force sensor from one measurement head to another measurement head every time when the measurement head is changed.

In accordance with a second aspect of the invention, there is provided a new optical measurement instrument comprising:

a measurement head being an optical interface of the optical measurement instrument with respect to a sample to be measured and/or excited, first mechanical support elements arranged to support a sample well plate to be received, second mechanical support elements arranged to support the measurement head and to allow a distance from the measurement head to the sample well plate to be changed, a controller arranged make, in a situation in which the sample well plate is placed on the first mechanical support elements, the second mechanical support elements to move the measurement head towards the sample well plate and, as a response to a situation in which the measurement head touches the sample well plate, to move the measurement head backwards away from the sample well plate with a pre-determined length of movement so as to provide a pre-determined distance between the measurement head and the sample well plate, and a sensor device arranged to detect, in the situation in which the sample well plate is placed on the first mechanical support elements, the situation in which the measurement head touches the sample well plate, wherein the sensor device is attached to the first mechanical support elements and arranged to detect, in the situation in which the sample well plate is placed on the first mechanical support elements, a mechanical effect occurring in the first mechanical support elements due to force directed by the measurement head to the sample well plate.

In accordance with a third aspect of the invention, there is provided a new method for controlling a measurement head of an optical measurement instrument, the measurement head being an optical interface of the optical measurement instrument with respect to a sample to be measured and/or excited, and the optical measurement instrument further comprising first mechanical support elements arranged to support a sample well plate to be received, and second mechanical support elements arranged to support the measurement head and to allow a distance from the measurement head to the sample well plate to be changed. The method according to the invention comprises:

moving the measurement head towards the sample well plate placed on the first mechanical support elements, detecting, with a sensor device attached to the first mechanical support elements, a mechanical effect occurring in the first mechanical support elements in order to detect a situation in which the measurement head touches the sample well plate, and as a response to the situation in which the measurement head touches the sample well plate, moving the measurement head backwards away from the sample well plate with a pre-determined length of movement so as to provide a pre-determined distance between the measurement head and the sample well plate.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verb "to comprise" is used in this document as an open limitation that does not exclude the existence of also unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which.

DESCRIPTION OF THE EMBODIMENTS

Figure 1A:
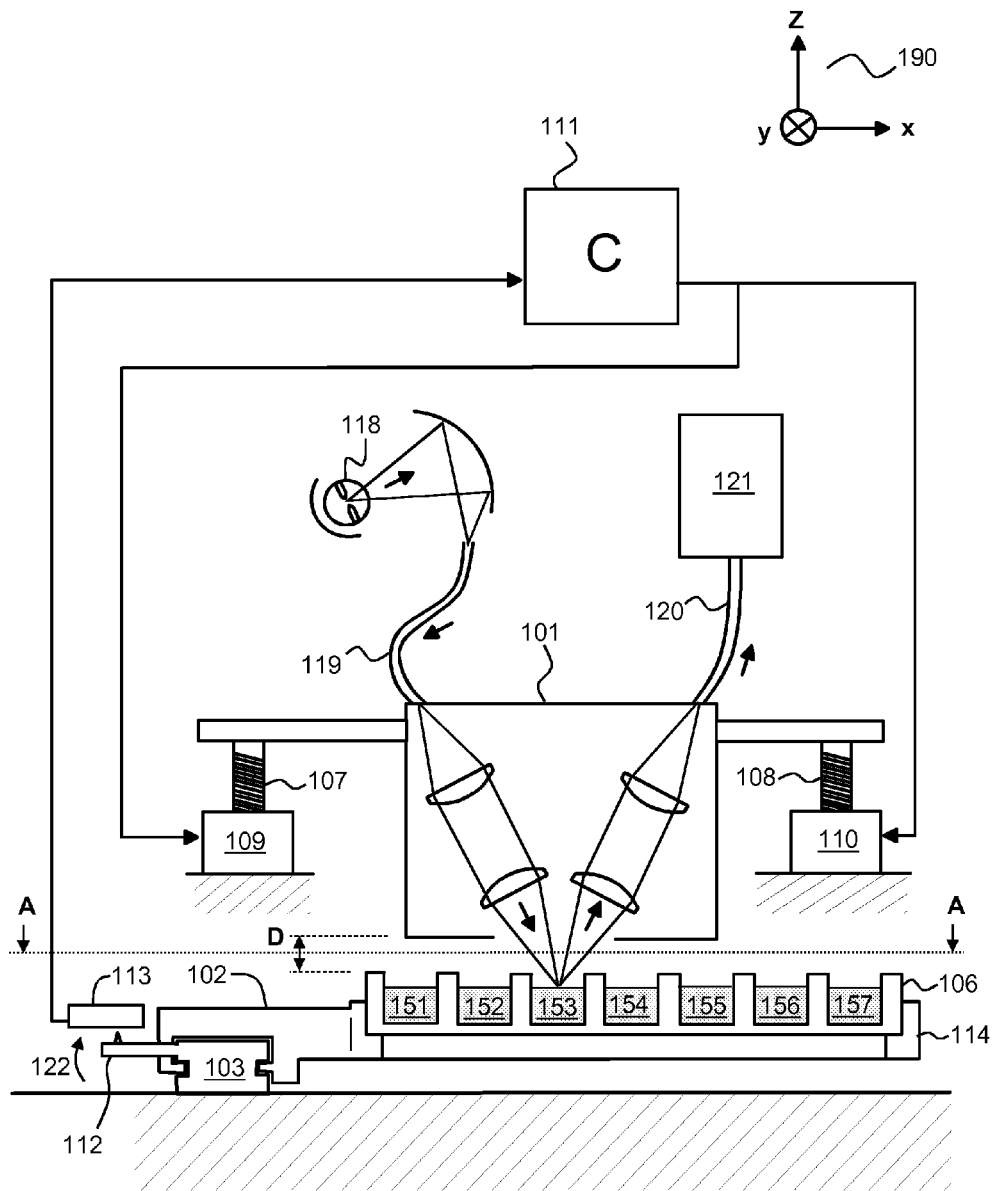
FIG. 1a shows a schematic illustration of an optical measurement instrument comprising an arrangement according to an embodiment of the invention for controlling a measurement head of the optical measurement instrument.
Figure 1B:
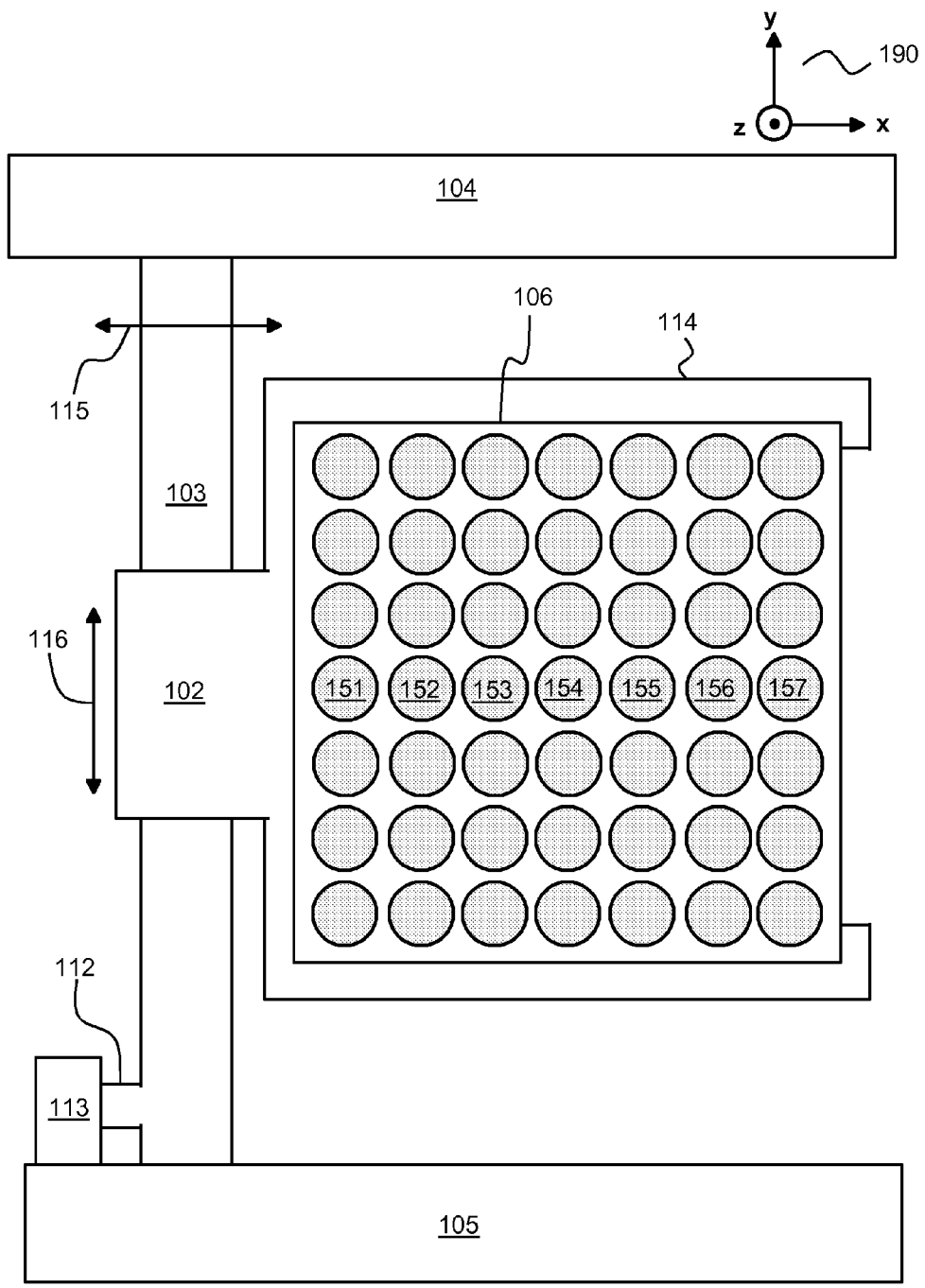
FIG. 1b shows a schematic illustration of a view seen downwards from line A-A of FIG. 1a, FIG. 2 shows a schematic illustration of an optical measurement instrument comprising an arrangement according to an embodiment of the invention for controlling a measurement head of the optical measurement instrument.

FIG. 1a shows a schematic illustration of an optical measurement instrument comprising an arrangement according to an embodiment of the invention for controlling a measurement head of the optical measurement instrument. FIG. 1b shows schematic illustration of a view seen downwards from line A-A of FIG. 1a. The optical measurement instrument comprises first mechanical support elements arranged to support a sample well plate 106, e.g. a microtitration plate. Samples 151, 152, 153, 154, 155, 156, 157 to be measured are stored in sample wells that are built on the sample well plate 106. The first mechanical support elements comprise a support rail 103 and guide elements 104 and 105 shown in FIG. 1b. The support rail 103 is supported relative to a body of the optical measurement instrument with the aid of the guide elements 104 and 105 in such a manner that the support rail is movable in the directions of a two-headed arrow 115 shown in FIG. 1b. The first mechanical support elements comprise a sledge 114 capable of receiving the sample well plate 106. The sledge is connected with the aid of a part 102 of the first mechanical support elements to the support rail 103 in such a manner that the sledge is capable of sliding along the support rail in the longitudinal direction of the support rail, i.e. the sledge is movable in the directions of a two-headed arrow 116 shown in FIG. 1b. Hence, the samples stored in the sample wells of the sample well plate 106 are movable in the xy-plane defined by a coordinate system 190. Due to the fact that the samples are movable in the xy-plane, the samples can be measured in a temporally successive manner so that each sample is in turn the sample that is currently being measured.

The optical measurement instrument comprises an excitation light source 118 that can be for example a flash lamp such as a xenon flash lamp. The excitation light produced by the excitation light source is focused with a concave mirror to a light guide 119 that can be e.g. a fiber bundle. The light guide 119 is connected to a measurement head 101 that comprises two channels, one for the excitation beam and another for an emission beam emitted by the sample 153 being measured. The measurement head 101 comprises plano-convex lenses arranged to focus the excitation beam to the sample 153 being measured and to collect the emission beam from the sample 153. The emission beam is conducted via a light guide 120 to a detector 121 arranged to detect the emission beam emitted by the sample 153 and to produce a detection signal responsive to the detected emission beam. The detector can be for example a photodiode or a photomultiplier tube.

The optical measurement instrument comprises second mechanical support elements arranged to support the measurement head 101 and to allow a distance D from the measurement head to the sample well plate 106 to be changed. The second mechanical support elements comprise threaded rods 107 and 108. Counterparts 109 and 110 of the threaded rod may comprises, for example, servomotors arranged to move the measurement head 101 in the positive or negative z-direction of the co-ordinate system 190.

The arrangement according to an embodiment of the invention for controlling the measurement head 101 comprises a controller 111 arranged make the second mechanical support elements 107-110 to move the measurement 101 head towards the sample well plate 106 and, as a response to a situation in which the measurement head touches the sample well plate, to move the measurement head backwards away from the sample well plate with a pre-determined length of movement so as to provide a desired pre-determined distance between the measurement head and the sample well plate. The arrangement further comprises a sensor device attached to the first mechanical support elements and arranged to detect a mechanical effect occurring in the first mechanical support elements 102-105 due to force directed by the measurement head 101 to the sample well plate 106 in order to detect the situation in which the measurement head touches the sample well plate.

The sensor device comprises an overhang 112 attached to the support rail 103 and arranged to be turned as a response to torsion of the support rail due to the force directed by the measurement head to the sample well plate. The sensor device comprises a counterpart 113 that is connected to the guide element 105 shown in FIG. 1b. The counterpart 113 is preferably arranged to move in the positive or negative x-direction of the co-ordinate system 190 along with movements of the support rail 103. The overhang 112 comprises a contact point that makes an electrical contact with the counterpart 113 as a response to torsion of the support rail 113 due to the force directed by the measurement head to the sample well plate. An arrow 122 shown in FIG. 1a illustrates the movement of the contact point when the measurement head 101 pushes the sample well plate 106. Hence, the sensor device shown in FIG. 1a comprises actually an electrical contactor the electrical conductivity state of which is arranged to be changed as a response to a situation in which a part of the first mechanical support elements 102-105 is bent due to the force directed by the measurement head to the sample well plate, the mechanical effect to be detected being the bending of the part of the first mechanical support elements. It is also possible that the sensor device comprises a pressure force sensor placed between the overhang 112 and the counterpart 113.

Figure 2:
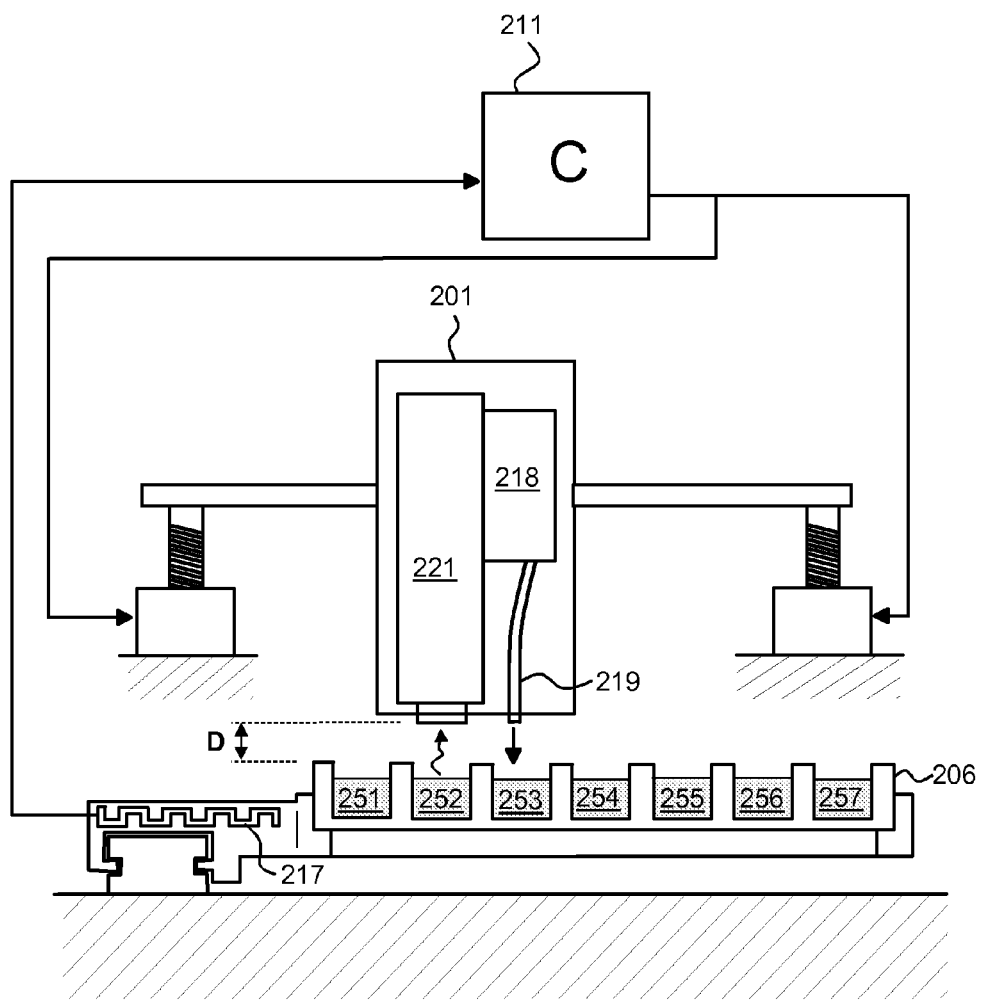

FIG. 2 shows a schematic illustration of an optical measurement instrument comprising an arrangement according to an embodiment of the invention for controlling a measurement head of the optical measurement instrument. Samples 251, 252, 253, 254, 255, 256, 257 to be measured are stored in sample wells that are built on a sample well plate 206. The optical measurement instrument comprises first mechanical support elements arranged to support the sample well plate 206. The first mechanical support elements can be similar to those of the optical measurement instrument shown in FIGS. 1a and 1b.

A measurement head 201 comprises an excitation light source 218 that is a laser source and a detector 221 that is preferably a photomultiplier tube. An excitation beam is conducted with a light guide 219 to the sample 253 being excited. The detector 221 is arranged to detect an emission beam emitted by the sample 252 being measured and to produce a detection signal responsive to the detected emission beam.

The optical measurement instrument comprises second mechanical support elements arranged to support the measurement head 201 and to allow a distance D from the measurement head to the sample well plate 206 to be changed. The second mechanical support elements can be similar to those of the optical measurement instrument shown in FIGS. 1a and 1b.

The arrangement according to an embodiment of the invention for controlling the measurement head 201 comprises a controller 211 arranged make the second mechanical support elements to move the measurement 201 head towards the sample well plate 206 and, as a response to a situation in which the measurement head touches the sample well plate, to move the measurement head backwards away from the sample well plate with a pre-determined length of movement so as to provide a desired pre-determined distance between the measurement head and the sample well plate. The arrangement further comprises a sensor device attached to the first mechanical support elements and arranged to detect a mechanical effect occurring in the first mechanical support elements due to force directed by the measurement head 201 to the sample well plate 206 in order to detect the situation in which the measurement head touches the sample well plate.

The sensor device comprises a wire strain gauge 217 attached to the first mechanical support elements. The wire strain gauge is used for generating a signal responsive to deformation taking place in a part of the first mechanical support elements due to the force directed by the measurement head to the sample well plate. The mechanical effect to be detected is therefore a change of mechanical strain occurring in the first mechanical support elements due to the force directed by the measurement head to the sample well plate.

Referring to FIGS. 1 and 2, an optical measurement instrument according to an embodiment of the invention comprises:
- a measurement head 101, 201 that is an optical interface of the optical measurement instrument with respect to a sample to be measured and/or excited,
- first mechanical support elements 102-105 arranged to support a sample well plate 106,
- second mechanical support elements 107-110 arranged to support the measurement head and to allow a distance D from the measurement head to the sample well plate to be changed,
- a controller 111, 211 arranged make the second mechanical support elements to move the measurement head towards the sample well plate and, as a response to a situation in which the measurement head touches the sample well plate, to move the measurement head backwards away from the sample well plate with a pre-determined length of movement so as to provide a pre-determined distance between the measurement head and the sample well plate, and
- a sensor device 112, 113, 217 arranged to detect the situation in which the measurement head touches the sample well plate, wherein the sensor device is attached to the first mechanical support elements and arranged to detect a mechanical effect occurring in the first mechanical support elements due to force directed by the measurement head to the sample well plate.

Figure 3:
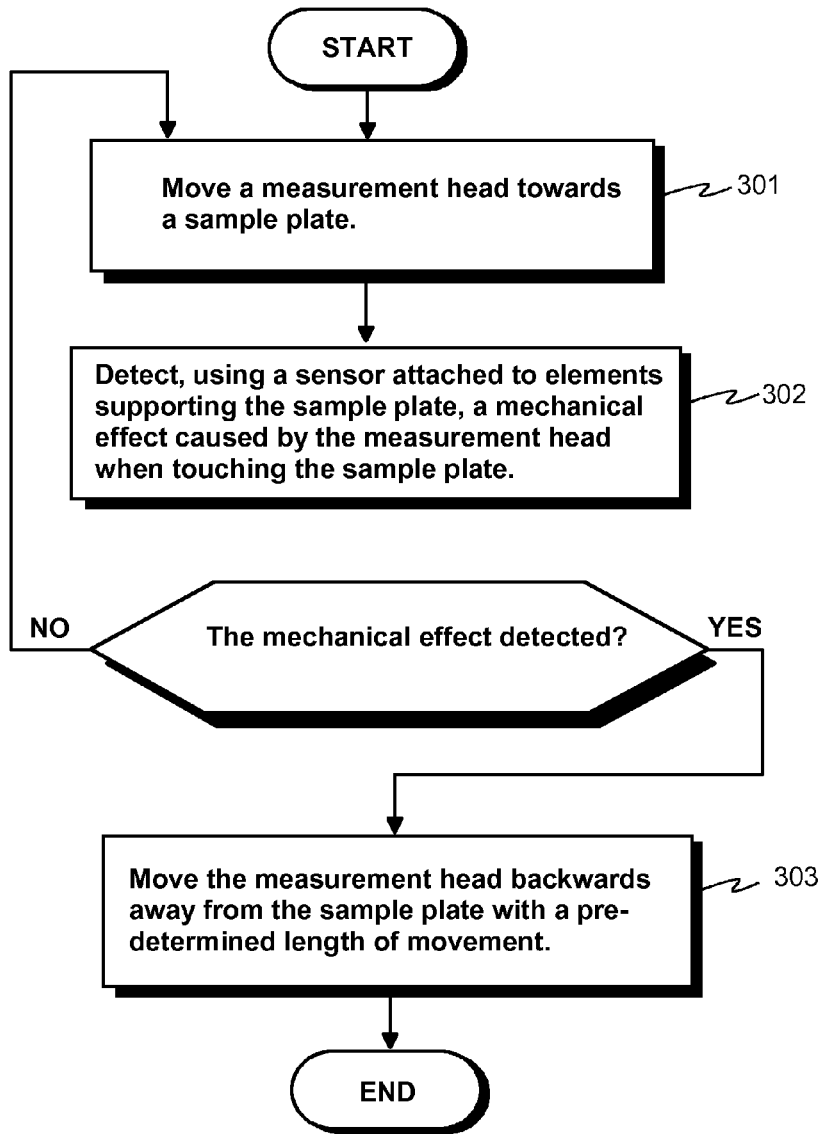
FIG. 3 shows a flow chart of a method according to an embodiment of the invention for controlling a measurement head of an optical measurement instrument.

FIG. 3 shows a flow chart of a method according to an embodiment of the invention for controlling a measurement head of an optical measurement instrument that further comprises first mechanical support elements arranged to support a sample well plate to be received, and second mechanical support elements arranged to support the measurement head and to allow a distance from the measurement head to the sample well plate to be changed. The method comprises:
- moving in a phase 301 the measurement head towards the sample well plate,
- detecting in phase 302 with the aid of a sensor device attached to the first mechanical support elements a mechanical effect occurring in the first mechanical support elements in order to detect a situation in which the measurement head touches the sample well plate, and
- as a response to the situation in which the measurement head touches the sample well plate, moving in a phase 303 the measurement head backwards away from the sample well plate with a pre-determined length of movement so as to provide a desired pre-determined distance between the measurement head and the sample well plate.

In a method according to an embodiment of the invention, the mechanical effect occurring in the first mechanical support elements is detected with a wire strain gauge attached to the first mechanical support elements, the mechanical effect to be detected being a change of mechanical strain occurring in the first mechanical support elements due to the force directed by the measurement head to the sample well plate.

In a method according to an embodiment of the invention, the mechanical effect occurring in the first mechanical support elements is detected with an electrical contactor the electrical conductivity state of which is changed as a response to a situation in which a part of the first mechanical support elements is bent due to the force directed by the measurement head to the sample well plate, the mechanical effect to be detected being the bending of the part of the first mechanical support elements.

In a method according to an embodiment of the invention, the first mechanical support elements comprise a support rail and a sledge capable of receiving the sample well plate and capable of sliding along the support rail in the longitudinal direction of the support rail, and the mechanical effect occurring in the first mechanical support elements is detected with an overhang attached to the support rail and arranged to be turned as a response to torsion of the support rail due to the force directed by the measurement head to the sample well plate, the mechanical effect to be detected being the turning of the overhang.

The specific examples provided in the description given above should not be construed as limiting. Therefore, the invention is not limited merely to the embodiment described above.

What is claimed is:

1. An arrangement for controlling a measurement head (101, 201) of an optical measurement instrument, the optical measurement instrument comprising first mechanical support elements (102-105) arranged to support a sample well plate (106, 206) to be received, and second mechanical support elements (107-110) arranged to support the measurement head and to allow a distance (D) from the measurement head to the sample well plate to be changed, the arrangement comprising:
   a controller (111, 211) arranged to make, in a situation in which the sample well plate is placed on the first mechanical support elements, the second mechanical support elements to move the measurement head towards the sample well plate and, as a response to a situation in which the measurement head touches the sample well plate, to move the measurement head backwards away from the sample well plate with a pre-determined length of movement so as to provide a pre-determined distance between the measurement head and the sample well plate, and
   a sensor device (112, 113, 217) arranged to detect, in the situation in which the sample well plate is placed on the first mechanical support elements, the situation in which the measurement head touches the sample well plate,
   wherein the sensor device is attached to the first mechanical support elements and arranged to detect, in the situation in which the sample well plate is placed on the first mechanical support elements, a mechanical effect occurring in the first mechanical support elements due to force directed by the measurement head to the sample well plate.

2. The arrangement according to claim 1, wherein the sensor device comprises a wire strain gauge (217) attached to the first mechanical support elements, the mechanical effect to be detected being a change of mechanical strain occurring in the first mechanical support elements due to the force directed by the measurement head to the sample well plate.

3. The arrangement according to claim 1, wherein the sensor device comprises an electrical contactor (112, 113) the electrical conductivity state of which is arranged to be changed as a response to a situation in which a part of the first mechanical support elements is bent due to the force directed by the measurement head to the sample well plate, the mechanical effect to be detected being bending of the part of the first mechanical support elements.

4. The arrangement according to claim 3, wherein the first mechanical support elements comprise a support rail (103) and a sledge (114) capable of receiving the sample well plate and capable of sliding along the support rail in a longitudinal direction of the support rail, the sensor device comprising an overhang (112) attached to the support rail and arranged to be turned as a response to torsion of the support rail due to the force directed by the measurement head to the sample well plate, the mechanical effect to be detected being turning of the overhang.

5. An optical measurement instrument comprising:
a measurement head (101, 201),
first mechanical support elements (102-105) arranged to support a sample well plate (106, 206) to be received, and
second mechanical support elements (107-110) arranged to support the measurement head and to allow, in a situation in which the sample well plate is placed on the first mechanical support elements, a distance from the measurement head to the sample well plate to be changed,
wherein the optical measurement instrument further comprises the arrangement according to claim 1 for controlling, in the situation in which the sample well plate is placed on the first mechanical support elements, the position of the measurement head relative to the sample well plate.

6. A method for controlling a measurement head of an optical measurement instrument, and the optical measurement instrument comprising first mechanical support elements arranged to support a sample well plate to be received, and second mechanical support elements arranged to support the measurement head and to allow a distance from the measurement head to the sample well plate to be changed, the method comprising:
moving (301) the measurement head towards the sample well plate placed on the first mechanical support elements,
detecting (302) a situation in which the measurement head touches the sample well plate, and
as a response to the situation in which the measurement head touches the sample well plate, moving (303) the measurement head backwards away from the sample well plate with a pre-determined length of movement so as to provide a pre-determined distance between the measurement head and the sample well plate,
wherein the situation in which the measurement head touches the sample well plate is detected by detecting (301), with a sensor device attached to the first mechanical support elements, a mechanical effect occurring in the first mechanical support elements due to force directed by the measurement head to the sample well plate.

7. The method according to claim 6, wherein the mechanical effect occurring in the first mechanical support elements is detected with a wire strain gauge attached to the first mechanical support elements, the mechanical effect to be detected being a change of mechanical strain occurring in the first mechanical support elements due to the force directed by the measurement head to the sample well plate.

8. The method according to claim 6, wherein the mechanical effect occurring in the first mechanical support elements is detected with an electrical contactor the electrical conductivity state of which is changed as a response to a situation in which a part of the first mechanical support elements is bent due to the force directed by the measurement head to the sample well plate, the mechanical effect to be detected being bending of the part of the first mechanical support elements.

9. The method according to claim 6, wherein the first mechanical support elements comprise a support rail and a sledge capable of receiving the sample well plate and capable of sliding along the support rail in a longitudinal direction of the support rail, and the mechanical effect occurring in the first mechanical support elements is detected with an overhang attached to the support rail and arranged to be turned as a response to torsion of the support rail due to the force directed by the measurement head to the sample well plate, the mechanical effect to be detected being turning of the overhang.

10. The arrangement according to claim 1, wherein the sample well plate is a microtitration plate.

11. The arrangement according to claim 1, wherein samples stored in the sample well plate are movable in an xy plane.

12. The arrangement according to claim 1, wherein the second mechanical support elements comprise threaded rods.

13. The arrangement according to claim 12, wherein counterparts of the threaded rods comprise servomotors arranged to move the measurement head in a positive or negative z direction.

14. The method according to claim 6, wherein the sample well plate is a microtitration plate.

15. The method according to claim 6, wherein samples stored in the sample well plate are movable in an xy plane.

16. The method according to claim 6, wherein the second mechanical support elements comprise threaded rods.

17. The method according to claim 16, wherein counterparts of the threaded rods comprise servomotors arranged to move the measurement head in a positive or negative z direction.

* * * * *

UNITED STATES PATENT AND TRADEMARK OFFICE
CERTIFICATE OF CORRECTION

PATENT NO. : 8,542,349 B2  Page 1 of 1
APPLICATION NO. : 13/145652
DATED : September 24, 2013
INVENTOR(S) : Laitinen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 174 days.

Signed and Sealed this
Fifteenth Day of September, 2015

Michelle K. Lee
*Director of the United States Patent and Trademark Office*